United States Patent
Griffin et al.

(10) Patent No.: US 9,242,124 B2
(45) Date of Patent: Jan. 26, 2016

(54) LOW-TEMPERATURE PHASE-STABLE ACYL GLYCINATE COMPOSITIONS

(71) Applicant: RHODIA OPERATIONS, Paris (FR)

(72) Inventors: James Griffin, Jackson, NJ (US); Stewart Warburton, West Windsor, NJ (US); David Dobrowolski, Robbinsville, NJ (US)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/325,479

(22) Filed: Jul. 8, 2014

(65) Prior Publication Data

US 2015/0011456 A1    Jan. 8, 2015

Related U.S. Application Data

(60) Provisional application No. 61/843,604, filed on Jul. 8, 2013.

(51) Int. Cl.

| | | |
|---|---|---|
| *C11D 1/10* | (2006.01) | |
| *C11D 1/88* | (2006.01) | |
| *C11D 1/90* | (2006.01) | |
| *C11D 1/92* | (2006.01) | |
| *C11D 3/26* | (2006.01) | |
| *C11D 3/32* | (2006.01) | |
| *C11D 7/32* | (2006.01) | |
| *A61Q 5/02* | (2006.01) | |
| *A61Q 19/10* | (2006.01) | |
| *A61K 8/44* | (2006.01) | |
| *A61K 8/46* | (2006.01) | |

(52) U.S. Cl.
CPC ... *A61Q 5/02* (2013.01); *A61K 8/44* (2013.01); *A61K 8/466* (2013.01); *A61Q 19/10* (2013.01); *A61K 2800/596* (2013.01); *A61K 2800/5922* (2013.01)

(58) Field of Classification Search
CPC .............. C11D 1/10; C11D 1/88; C11D 1/90; C11D 1/92; C11D 3/2065; C11D 3/2075; C11D 3/26; C11D 3/32; C11D 7/32
See application file for complete search history.

(56) References Cited

U.S. PATENT DOCUMENTS

| | | | |
|---|---|---|---|
| 6,831,108 B2 | 12/2004 | Dahanayake et al. | |
| 7,384,898 B2 | 6/2008 | Koshti et al. | |
| 7,461,694 B2 | 12/2008 | Dahanayake et al. | |
| 8,501,808 B2 | 8/2013 | Dasgupta et al. | |
| 2003/0181341 A1 | 9/2003 | Yoshimi | |
| 2005/0096249 A1 | 5/2005 | Jonas et al. | |
| 2012/0009127 A1* | 1/2012 | Dasgupta et al. | 424/43 |
| 2012/0010115 A1 | 1/2012 | Mitchell et al. | |
| 2013/0029899 A1 | 1/2013 | Hermanson et al. | |
| 2013/0030197 A1 | 1/2013 | Harichian et al. | |
| 2013/0210696 A1* | 8/2013 | Vethamuthu et al. | 510/490 |

FOREIGN PATENT DOCUMENTS

EP    1000606 A2    5/2000

OTHER PUBLICATIONS

Clariant Iberica Produccion, S.A., Hostapon SG 1907/2006 Safety Data Sheet, Jul. 6, 2009.
Ajinomoto, Amilite GCS-12K MSDS, Apr. 14, 2009.
Estee Lauder Pty Ltd, Potassium Cocoyl Glycinate MSDS, Nov. 2008.
Unilever Australia Limited, Sodium Cocoyl Glycinate MSDS, Jun. 2007.

* cited by examiner

*Primary Examiner* — Brian P Mruk

(57) ABSTRACT

Low-temperature stable concentrate compositions comprising an acyl glycinate present in an amount greater than 70 wt % by weight of the composition; and b) at least one of a zwitterionic surfactant or an amphoteric surfactant present in an amount greater than 0.1 wt % by weight of the composition, wherein the concentrate is low temperature stable.

19 Claims, No Drawings

LOW-TEMPERATURE PHASE-STABLE ACYL GLYCINATE COMPOSITIONS

CROSS REFERENCE TO RELATED APPLICATIONS

This application claims the benefit of U.S. Provisional Application Ser. No. 61/843,604, filed on Jul. 8, 2013, herein incorporated by reference.

FIELD OF THE INVENTION

This invention relates to personal and home care compositions, more particularly to concentrated acyl glycinate systems that are phase-stable at low temperatures.

BACKGROUND

Aqueous compositions containing acyl glycinates compositions are useful in personal care applications, such as shampoos, body wash, hand soap, lotions, creams, conditioners, shaving products, facial washes, neutralizing shampoos, and other skin treatment applications, in home care applications, such as liquid detergents, laundry detergents, hard surface cleansers, dish wash liquids, toilet bowl cleaners, and in other applications, such as oil field and agrochemical applications. Acyl glycinates, in particular cocoyl glycinates, impart excellent foaming properties and ultra-mild cleaning properties in personal and home care products. Additionally, acyl glycinates impart a non-oily feeling on skin and are usually associated with luxury personal and home care products.

In some personal care compositions, such as, for example, children's shampoos, it important that the composition not be harsh on skin. In other applications, such as facial washes and compositions for sensitive skin, it is important that the composition does not irritate the skin. Acyl glycinates impart these desirable properties in these applications and compositions, and are associated with high end personal and home care compositions and application Generally, however, acyl glycinates are negatively affected by low temperature; for example, sodium cocoyl glycinate has a Cloud Point of 17° C., and a freezing point of 13° C. Concentrated compositions containing high amounts of acyl glycinates are especially susceptible to low temperatures, generally, below 20° C. As a result of such exposure, these concentrated compositions can phase-separate, wherein some components precipitate out, making the compositions difficult to pump and handle in general.

Concentrated compositions containing high amounts of acyl glycinates are typically supplied to end-product formulators to incorporate into retail personal and home care compositions. Special handling precautions are utilized in transporting, processing and handling of acyl glycinate compositions to such formulators, due to their negative susceptibility to low temperatures. For example, often times end-product formulators have supplies of acyl glycinates shipped in temperature-controlled shipping containers to their plants. In some instances, end-product formulators further process and mix its supply of acyl glycinate, prior to incorporating the acyl glycinate into an end-use personal care product, if such supply was exposed to low temperatures, as the acyl glycinate concentrates are often times phase separated. Handling and, more specifically, pumping of acyl glycinate concentrates that are phase separated is difficult.

SUMMARY OF THE INVENTION

Accordingly, there is a need for low-temperature phase-stable compositions of acyl glycinate, for which formulators can avoid special shipping, storage, and handling. In particular, there is a need for low temperature phase-stable compositions of acyl glycinate concentrates or concentrate compositions, which needs little or no special handling, shipping and storage restrictions such as, for example, the requirement that the acyl glycinate concentrates be stored and transported above 20° C., more typically above 25° C., even more typically, above 35° C. The ability for acyl glycinate concentrates to be transported, stored and/or handled below 35° C., more typically below 25° C., even more typically, below 20° C. without phase-separating, is desirable. Further, imparting freeze-thaw stability on acyl glycinate concentrates is also desirable.

In one aspect, described herein are low-temperature phase-stable concentrate composition comprising: a) an acyl glycinate present in an amount greater than 10 wt %, by weight of the composition; and b) at least one of a zwitterionic surfactant or an amphoteric surfactant present in an amount greater than 0.1 wt % by weight of the composition, wherein the concentrate is phase-stable at a temperature less than or equal to 17° C.

In some embodiments, the acyl glycinate is of formula (I):

$$RC(O)NHCH_2CO_2X \qquad (I),$$

wherein R is a $C_9$-$C_{23}$ alkyl Group, and X is a cation or H.

The cation can be any suitable cation, typically, sodium, potassium, or ammonium. The R group is, in one embodiment, a $C_8$-$C_{18}$ group, while in other embodiments, R is a $C_{10}$-$C_{14}$ group. It understood that the term "acyl glycinate" also encompasses acyl glycinate salts such as, e.g., sodium acyl glycinate.

Typically, the acyl glycinate is present in an amount having an upper limit of 80 wt % by weight of the concentrated composition. In other embodiments, the acyl glycinate is present in an amount having an upper limit of 85 wt % by weight of the composition, or having an upper limit of 90 wt % by weight of the composition. In a further embodiment, the acyl glycinate is present in an amount having an upper limit of 95-wt % by weight of the composition.

The at least one zwitterionic surfactant or amphoteric surfactant can be an alkyl betaine surfactant, an alkyl hydroxyl sulfobetaine surfactant, or an alkyl sulfobetaine surfactant, or an alkylamphoacetate, or a salt of any of the foregoing. In another embodiment, the at least one zwitterionic surfactant or amphoteric surfactant is selected from an alkyl betaine surfactant or salt thereof, an alkyl hydroxyl sulfobetaine surfactant or salt thereof, or an alkyl sulfobetaine surfactant or salt thereof. In some embodiments, the zwitterionic surfactant or amphoteric surfactant component can be a combination of two or more of an alkyl betaine surfactant, an alkyl hydroxyl sulfobetaine surfactant, and an alkyl sulfobetaine surfactant.

The at least one zwitterionic surfactant or amphoteric surfactant is present in an amount greater than 0.5 wt % by weight of the composition, or present in an amount greater than 1 wt % by weight of the composition, or present in an amount greater than 2 wt % by weight of the composition. In another embodiment, The at least one zwitterionic surfactant is present in an amount greater than 0.5 wt % by weight of the composition, or present in an amount greater than 1 wt % by weight of the composition, or present in an amount greater than 2 wt % by weight of the composition.

In other embodiments, the at least one zwitterionic surfactant or amphoteric surfactant is present in an amount greater than 5 wt % by weight of the composition. In another embodiment, the at least one zwitterionic surfactant or amphoteric surfactant is present in an amount greater than 7 wt % by weight of the composition. In a further embodiment, the at least one zwitterionic surfactant or amphoteric surfactant is present in an amount greater than 9 wt % by weight of the composition. In yet a further embodiment, the at least one zwitterionic surfactant or amphoteric surfactant is present in an amount greater than 10 wt % by weight of the composition.

In another embodiment, the at least one zwitterionic surfactant or amphoteric surfactant is selected from alkyl betaines, amidopropyl betaines, and alkyl hydroxyl sulfobetaine, alkyl sulfobetaine, alkyl amphocarboxy glycinates salts, alkyl amphocarboxypropionate salts, alkyl amphodipropionate salts, alkyl amphodiacetate salts, alkyl amphoglycinate salts, alkyl amphopropionate salts, alkyl iminopropionate salts, alkyl iminodipropionate salts, and alkyl amphopropylsulfonate salts, or mixtures thereof.

The amphoteric surfactant can also be selected from cocoamphoacetate, cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, stearoamphoacetate, salts thereof or mixtures thereof.

In a further aspect, described herein are personal care compositions comprising water and the concentrate compositions containing acyl glycinate as described herein.

In a further aspect, described herein are methods for storing a concentrated acyl glycinate composition by: a) obtaining a concentrated acyl glycinate composition comprising greater than about 10 wt %, by weight of composition, of acyl glycinate; and b) contacting a surfactant component comprising at least one of a zwitterionic surfactant or amphoteric surfactant with the concentrated acyl glycinate composition, whereby the concentrated acyl glycinate composition is phase-stable at a temperature less than or equal to 17° C.

In some embodiments, the resulting mixture is phase-stable at temperature of less than 8° C. In other embodiments, the resulting mixture is phase-stable at temperature of less than 4° C.

In another aspect, described herein are methods for imparting low temperature phase-stability to a concentrated acyl glycinate composition comprising: contacting a surfactant component comprising at least one of a zwitterionic surfactant or an amphoteric surfactant to a concentrated acyl glycinate composition, forming a resulting mixture, wherein the concentrated acyl glycinate composition comprises acyl glycinate in an amount greater than 10 wt %, by weight of the composition, whereby the resulting mixture is phase-stable at a temperature less than or equal to 10° C. In some embodiments, the resulting mixture is phase-stable at temperature of less than 8° C. In other embodiments, the resulting mixture is phase-stable at temperature of less than 4° C. In other embodiments, the resulting mixture is phase-stable at temperature of less than 2° C. In other embodiments, the resulting mixture is phase-stable at temperature of less than 0° C.

In yet another aspect, described herein are methods of imparting freeze-thaw stability to an acyl glycinate concentrate composition comprising the steps of: obtaining an acyl glycinate concentrate composition comprising acyl glycinate in an amount greater than 10 wt %, by weight of the composition; and contacting the acyl glycinate concentrate composition with a surfactant component comprising at least one of a zwitterionic surfactant or an amphoteric surfactant, wherein the surfactant component is present in an amount greater than 0.1% by weight of the composition, effective to impart freeze-thaw stability to the composition.

DETAILED DESCRIPTION OF INVENTION AND PREFERRED EMBODIMENTS

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, cyclohexyl.

As used herein, the term "alkenyl" means an unsaturated straight chain, branched chain, or cyclic hydrocarbon radical having at least one carbon-carbon double bond per radical, such as for example, propenyl, butenyl.

As used herein, the term "alkynyl" means an unsaturated straight chain, branched chain, or cyclic hydrocarbon radical having at least one carbon-carbon triple bond per radical, such as for example, propynyl, butynyl.

As used herein, the term "alkoxyl" means a saturated or unsaturated straight chain or branched chain ether radical, such as for example, ethoxy, propoxy, isopropoxy, butoxy, the term "alkoxylated" or "alkoxylate" in reference to an organic moiety means that the moiety is substituted with one or more alkoxy groups, typically with a polyether group, such as, for example a poly(ethoxy), poly(propoxy) or poly(ethoxypropoxy) group, the term "propoxylated" in reference to an organic moiety means that the moiety is substituted with a at least one propoxyl unit, and the term "butoxylated" in reference to an organic moiety means that the moiety is substituted with at least one butoxyl unit. As used herein, the notation "(n)", wherein n is an integer, in reference to the polyalkoxy group of an alkoxylated moiety indicates the number of alkoxy units in the polyalkoxy group. For example, "propoxylated (5) decyl alcohol" means decyl alcohol alkoxylated with 5 moles of propoxyl units per mole of decyl alcohol and butoxylated (3) dodecyl alcohol means decyl alcohol alkoxylated with 3 moles of butoxyl units per mole of decyl alcohol.

As used herein, the terminology "($C_n$-$C_m$)" in reference to an organic group, wherein n and m are each integers, indicates that the group may contain from n carbon atoms to m carbon atoms per group.

As used herein, the terminology "alcohols" refers to saturated or unsaturated fatty alcohols, typically ($C_8$-$C_{24}$)alcohols, such as, for example, hexyl alcohol, ocyl alcohol, decyl alcohol, undecyl alcohol, dodecyl alcohol, tridecyl alcohol, pentadecyl alcohol, hexadecyl alcohol, heptadecyl alcohol, octadecyl alcohol, nonadecyl alcohol, eicosyl alcohol, ducosyl alcohol, tricosyl alcohol, as well as mixtures thereof.

As used herein, the term "phase stable" (or "phase-stability") means that no visible phase separation of the acyl glycinate from the aqueous medium is observed at or below a specified ambient temperature. In another embodiment, the term "phase stable" (or "phase-stability") means that no visible phase separation of a precipitate from the aqueous medium is observed at or below a specified ambient temperature.

Generally, a phase-stable system is one in which the system is homogenous, i.e., no phase separation of components. In some embodiments, the specified ambient temperature is 20° C. or 19° C. In other embodiments, the specified ambient temperature is 18° C. In some other embodiments, the specified ambient temperature is 17° C., 16° C., 15° C., 14° C., or 13° C. In alternative embodiments, the specified ambient temperature is 12° C., 10° C., 8° C., 6° C., or 5° C. In other embodiments, the specified ambient temperature is 4° C., 3° C., 2° C., or 1° C. In yet other embodiments, the specified ambient temperature is 0.5° C. or 0.1° C. In further embodiments, the specified ambient temperature is 0° C., −0.5° C., −1° C., −2° C., −3° C., −4° C. or −5° C. Phase separation can occur, typically, at or below the Krafft point or cloud point, typically cloud point, of a surfactant mixture, but above the freezing point. In some embodiments, the phase-stable concentrate composition remains a homogenous liquid down to 4° C. and recovers to a clear homogeneous liquid at 25° C. In some embodiments, the phase-stable concentrate composition remains a homogenous liquid down to −2° C., 0° C. or 2° C. and recovers to a clear homogeneous liquid at 25° C. or ambient temperature. In some other embodiments, the phase-stable concentrate composition remains a homogenous liquid below 4° C. and recovers to a clear homogeneous liquid at 25° C. or ambient temperature.

Freeze-thaw (sometimes herein referred to as "F/T") mean a freezing then thawing process. A surfactant composition during the thawing process of a freeze-thaw process often times cannot recover to form the same phase-stable composition as prior to the F/T process; as a result, after thawing, the surfactant composition contains precipitates or becomes hazy or turbid. The term "freeze-thaw stability" or being "freeze-thaw stable" is generally understood to mean that the composition or formulation does not remain a gel or contain precipitates after one or more F/T cycles. In some embodiments, the phase stable concentrate composition described herein is Freeze Thaw stable, wherein the concentrate composition is cooled to down to −14° C. and at 25° C. is recoverable to a homogeneous liquid, typically a clear homogenous liquid, (i.e., does not gel or contain precipitates once heated back up to 25° C. or ambient temperature). In some embodiments, the phase stable concentrate composition described herein is Freeze-Thaw stable, meaning the concentrate composition is recoverable to a homogeneous liquid at room temperature (i.e., does not gel or contain precipitates) after the composition is cooled to down to below 2° C., in some embodiments, below 0° C., in some other embodiments, below −4° C., in other embodiments, below −8° C., in further embodiments, below −10° C., in yet other embodiments, below −14° C.

In one embodiment, the concentrated acyl glycinate composition of the present invention comprises an upper limit of 99.99 wt %, based on weight of the concentrated composition, of at least one acyl glycinate. In another embodiment, the concentrated composition of the present invention comprises an upper limit 99.9 wt %, based on weight of the concentrated composition, of at least one acyl glycinate. In another embodiment, the concentrated composition of the present invention comprises an upper limit 99 wt %, based on weight of the concentrated composition, of at least one acyl glycinate. In another embodiment, the concentrated composition of the present invention comprises an upper limit 98 wt %, based on weight of the concentrated composition, of at least one acyl glycinate. In another embodiment, the concentrated composition of the present invention comprises an upper limit 96 wt %, based on weight of the concentrated composition, of at least one acyl glycinate. The wt % of acyl glycinates is based on an active weight basis.

In yet another embodiment, the concentrated composition of the present invention comprises an upper limit 94 wt %, based on weight of the concentrated composition, of at least one acyl glycinate. In another embodiment, the concentrated composition of the present invention comprises an upper limit 92 wt %, based on weight of the concentrated composition, of at least one acyl glycinate. In another embodiment, the concentrated composition of the present invention comprises an upper limit 90 wt %, based on weight of the concentrated composition, of at least one acyl glycinate. In another embodiment, the concentrated composition of the present invention comprises an upper limit of 80 wt %, based on weight of the concentrated composition, of at least one acyl glycinate. The wt % of acyl glycinates are on an active weight basis.

In another embodiment, the concentrated composition of the present invention comprises a lower limit of 50 wt % or 45 wt %, based on weight of the concentrated composition, of at least one acyl glycinate. In another embodiment, the concentrated composition of the present invention comprises a lower limit of 40 wt % or 35 wt %, based on weight of the concentrated composition, of at least one acyl glycinate. In another embodiment, the concentrated composition of the present invention comprises a lower limit of 30 wt %, 28 wt %, 26 wt %, 24 wt %, or 22 wt % based on weight of the concentrated composition, of at least one acyl glycinate. In a further embodiment, the concentrated composition of the present invention comprises a lower limit of 21 wt %, based on weight of the concentrated composition, of at least one acyl glycinate. In yet another embodiment, the concentrated composition of the present invention comprises a lower limit of 20 wt %, based on weight of the concentrated composition, of at least one acyl glycinate. In a further embodiment, the concentrated composition of the present invention comprises a lower limit of 19 wt %, based on weight of the concentrated composition, of at least one acyl glycinate. In a further embodiment, the concentrated composition of the present invention comprises a lower limit of 18 wt %, 16 wt %, 15 wt %, 14 wt %, 13 wt %, 12 wt %, 11 wt %, 10 wt % or 9 wt %, based on weight of the concentrated composition, of at least one acyl glycinate. In yet another embodiment, the concentrated composition of the present invention comprises a lower limit of 70 wt %, based on weight of the concentrated composition, of at least one acyl glycinate. The wt % of the acyl glycinates is on an active weight basis.

In one embodiment, the acyl glycinate is of formula (I):

$$RC(O)NHCH_2CO_2X \qquad (I),$$

wherein R is a $C_8$-$C_{22}$ alkyl group, and X is a cation or H.

Where X is a cation, the cation can be any suitable cation. In one embodiment, the cation is sodium, potassium, or ammonium. In another embodiment, the cation is lithium, alkyl ammonium, an alkaline earth metal such as calcium or magnesium, triethanolammonium, trialkylammonium, monoalkylammonium, dialkylammonium, isopropylammonium, monoethanolammonium, or diethanolammonium.

The R group is, in one embodiment, a $C_8$-$C_{18}$ group. In another embodiment, R is a $C_{10}$-$C_{14}$ group. In another embodiment, R is a $C_{12}$-$C_{14}$ group. In another embodiment, R is a $C_8$-$C_{14}$ group. In another embodiment, R is a $C_{12}$ group. In another embodiment, R is a $C_{10}$ group. In another embodiment, R is a $C_{14}$ group.

In one particular embodiment, the acyl glycinate is cocoyl glycinate or a cocoyl glycinate salt, more typically sodium cocoyl glycinate. In another particular embodiment, the acyl glycinate is lauryl glycinate or a lauryl glycinate salt, more typically, sodium lauryl glycinate. In another embodiment, the acyl glycinate is a mixture of cocoyl glycinate and lauryl glycinate. In another embodiment, the acyl glycinate is a mixture of at least two of: cocoyl glycinate, lauryl glycinate, cocoyl glycinate salt, and/or lauryl glycinate salt.

The at least one zwitterionic surfactant or amphoteric surfactant, in one embodiment, is an alkyl betaine, alkyl sulfobetaine, an alkyl dimethyl betaine, an alkyl amidopropyl hydroxy sulfobetaine or alkyl hydroxy sulfobetaine. In some embodiments, the wherein the alkyl group has an upper limit of 10 carbon atoms, or 12 carbon atoms, or 14 carbon atoms, 16 carbon atoms, 18 carbon atoms, 20 carbon atoms or 22 carbon atoms.

In one embodiment, the sulfobetaine of the present invention is of formula (II):

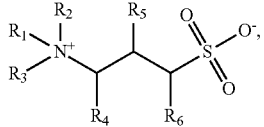

(II)

wherein R1 is an alkylamido group or a linear or branched alkyl group; R2 and R3 are individually hydrogen, a methyl group or a hydroxyethyl group; R4, R5 and R6 are individually hydrogen or a hydroxy group. In one embodiment, the alkyl group has greater than about 10 carbon atoms. In one embodiment, the alkyl group has greater than about 11, 12 or 13 carbon atoms. In another embodiment, the alkyl group has greater than about 14 or 16 carbon atoms.

In one embodiment, the alkylamido group has formula (III):

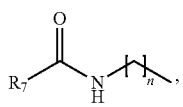

(III)

wherein R7 is a linear or branched alkyl group having greater than about 10 carbon atoms, wherein n is an integer from 2 to 5. In one embodiment, "n" is an integer of 3, and in another embodiment "n" is an integer of 4.

In some embodiments, zwitterionic surfactants include but are not limited to compounds having the formula:

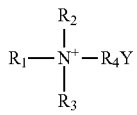

wherein R1 represents a hydrophobic moiety of alkyl, alkylarylalkyl, alkoxyalkyl, alkylaminoalkyl and alkylamidoalkyl, wherein alkyl represents a group that contains from about 10 to about 24 carbon atoms which may be branched or straight chained and which may be saturated or unsaturated. Representative long-chain alkyl groups include tetradecyl (myristyl), hexadecyl (cetyl), octadecenyl (oleyl), octadecyl (stearyl), docosenoic (erucyl) and the derivatives of tallow, coco, soya and rapeseed oils. The typical alkyl groups have from about 16 to about 22 carbon atoms. Representative of alkylamidoalkyl is alkylamidopropyl with alkyl being as described above.

R2 and R3 are independently an aliphatic chain (i.e. as opposed to aromatic at the atom bonded to the quaternary nitrogen, e.g., alkyl, arylalkyl, hydroxyalkyl, carboxyalkyl, and hydroxyalkyl-polyoxyalkylene, e.g. hydroxyethyl-polyoxyethylene or hydroxypropyl-polyoxypropylene) having from 1 to about 50 carbon atoms, in other embodiments from about 1 to about 20 carbon atoms, in other embodiments from about 1 to about 10 carbon atoms and in yet other embodiments from about 1 to about 6 carbon atoms in which the aliphatic group can be branched or straight chained, saturated or unsaturated. Exemplary alkyl chains are methyl, ethyl, preferred arylalkyl is benzyl, and preferred hydroxyalkyls are hydroxyethyl or hydroxypropyl, while preferred carboxyalkyls are acetate and propionate. Exemplary hydroxyalkyl-polyoxyalkylenes are hydroxyethyl-polyoxyethylene and hydroxypropyl-polyoxyethylene.

R4 is a hydrocarbyl radical (e.g. alkylene) with chain length 1 to 4. In one embodiment, R4 is a methylene or ethylene group.

Y is COO— or CH(OH)CH2SO3- or SO3-

In another embodiment, zwitterionic surfactants include, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group such as carboxyl, sulfonate, sulfate, phosphate or phosphonate. Specific examples of suitable zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

Specific non-limiting examples of suitable zwitterionic surfactants include the following structures:

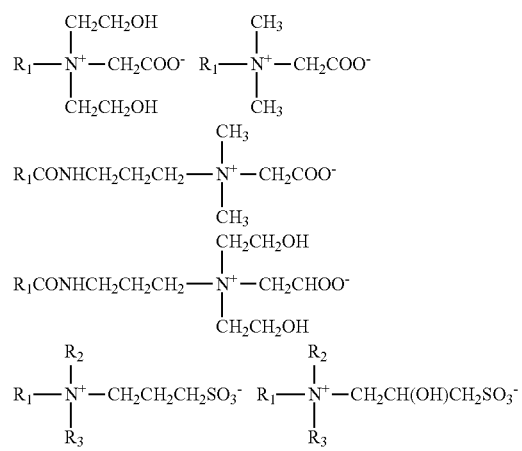

wherein R1 represents a hydrophobic moiety of alkyl, alkylarylalkyl, alkoxyalkyl, alkylaminoalkyl and alkylamidoalkyl, wherein alkyl represents a group that contains from about 10 to about 24 carbon atoms which may be branched or straight chained and which may be saturated or unsaturated. Representative long-chain alkyl groups include tetradecyl (myristyl), hexadecyl (cetyl), octadecenyl (oleyl), octadecyl (stearyl), docosenoic (erucyl) and the derivatives of tallow, coco, soya and rapeseed oils. The typical alkyl groups have from about 16 to about 22 carbon atoms. Representative of alkylamidoalkyl is alkylamidopropyl with alkyl being as described above.

R2 and R3 are independently an aliphatic chain (i.e. as opposed to aromatic at the atom bonded to the quaternary nitrogen, e.g., alkyl, arylalkyl, hydroxyalkyl, carboxyalkyl, and hydroxyalkyl-polyoxyalkylene, e.g. hydroxyethyl-polyoxyethylene or hydroxypropyl-polyoxypropylene) having from 1 to about 50 carbon atoms, in other embodiments from about 1 to about 20 carbon atoms, in other embodiments from about 1 to about 10 carbon atoms and in yet other embodiments from about 1 to about 6 carbon atoms in which the aliphatic group can be branched or straight chained, saturated or unsaturated.

Another example of a suitable zwitterionic surfactant selected is an amine oxide. This material has the following structure:

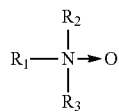

wherein R1 represents a hydrophobic moiety of alkyl, alkylarylalkyl, alkoxyalkyl, alkylaminoalkyl and alkylamidoalkyl, wherein alkyl represents a group that contains from about 10 to about 24 carbon atoms which may be branched or straight chained and which may be saturated or unsaturated. Representative long-chain alkyl groups include tetradecyl (myristyl), hexadecyl (cetyl), octadecenyl (oleyl), octadecyl (stearyl), docosenoic (erucyl) and the derivatives of tallow, coco, soya and rapeseed oils. The typical alkyl groups have from about 16 to about 22 carbon atoms. Representative of alkylamidoalkyl is alkylamidopropyl with alkyl being as described above.

R2 and R3 are independently an aliphatic chain (i.e. as opposed to aromatic at the atom bonded to the quaternary nitrogen, e.g., alkyl, arylalkyl, hydroxyalkyl, carboxyalkyl, and hydroxyalkyl-polyoxyalkylene, e.g. hydroxyethyl-polyoxyethylene or hydroxypropyl-polyoxypropylene) having from 1 to about 50 carbon atoms, in other embodiments from about 1 to about 20 carbon atoms, in other embodiments from about 1 to about 10 carbon atoms and in yet other embodiments from about 1 to about 6 carbon atoms in which the aliphatic group can be branched or straight chained, saturated or unsaturated.

Other representative zwitterionic surfactants include dihydroxyethyl tallow glycinate, propionates, oleamidopropyl betaine, and erucyl amidopropyl betaine.

Examples of amphoteric surfactants include but are not limited to those represented by the following formula:

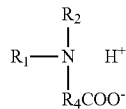

wherein R1 represents a hydrophobic moiety of alkyl, alkylarylalkyl, alkoxyalkyl, alkylaminoalkyl and alkylamidoalkyl, wherein alkyl represents a group that contains from about 10 to about 24 carbon atoms which may be branched or straight chained and which may be saturated or unsaturated. Representative long-chain alkyl groups include tetradecyl (myristyl), hexadecyl (cetyl), octadecenyl (oleyl), octadecyl (stearyl), docosenoic (erucyl) and the derivatives of tallow, coco, soya and rapeseed oils. The typical alkyl groups have from about 16 to about 22 carbon atoms. Representative of alkylamidoalkyl is alkylamidopropyl with alkyl being as described above.

R2 and R3 are independently an aliphatic chain (i.e. as opposed to aromatic at the atom bonded to the quaternary nitrogen, e.g., alkyl, arylalkyl, hydroxyalkyl, carboxyalkyl, and hydroxyalkyl-polyoxyalkylene, e.g. hydroxyethyl-polyoxyethylene or hydroxypropyl-polyoxypropylene) having from 1 to about 50 carbon atoms, in other embodiments from about 1 to about 20 carbon atoms, in other embodiments from about 1 to about 10 carbon atoms and in yet other embodiments from about 1 to about 6 carbon atoms in which the aliphatic group can be branched or straight chained, saturated or unsaturated.

Other specific non-limiting examples of amphoteric surfactants include the following structures:

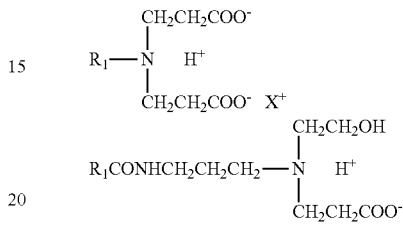

wherein R1 has been previously defined herein, and X+ is an inorganic cation such as Na+, K+, NH4+ associated with a carboxylate group or hydrogen atom in an acidic medium.

Useful zwitterionic and amphoteric surfactants include those disclosed in U.S. Pat. Nos. 6,831,108 B2 and 7,461,694 B2, which are incorporated herein by reference.

In another embodiment, the at least one zwitterionic surfactant or amphoteric surfactant is selected from: alkyl betaines and salts thereof, amidopropyl betaines and salts thereof, alkyl hydroxysulfobetaines and salts thereof, alkyl sulfobetaines and salts thereof, alkyl amphocarboxy glycinates and salts thereof, alkyl amphocarboxypropionate and salts thereof, alkyl amphodipropionate and salts thereof, alkyl amphoacetates and salts thereof, alkyl amphodiacetate and salts thereof, alkyl amphoglycinate and salts thereof, alkyl amphopropionate and salts thereof, alkyl iminopropionate and salts thereof, alkyl iminodipropionate and salts thereof, alkyl amphopropylsulfonate and salts thereof, or any mixtures thereof. In another embodiment, the at least one zwitterionic surfactant or amphoteric surfactant is selected from alkyl betaines or salts thereof, amidopropyl betaines or salts thereof, alkyl sulfobetaines or salts thereof, alkyl amphocarboxy glycinates or salts thereof, alkyl amphocarboxypropionates or salts thereof, alkyl amphodipropionates or salts thereof, alkyl amphoglycinates or salts thereof, alkyl amphopropionates or salts thereof, alkyl iminopropionates or salts thereof, alkyl iminodipropionates or salts thereof, alkyl amphopropylsulfonates or salts thereof, or mixtures thereof.

The amphoteric surfactant, in one embodiment, is selected from cocoamphoacetate, cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, stearoamphoacetate, salts thereof or mixtures thereof. In yet another embodiment, the amphoteric surfactant is selected from salts of cocoamphoacetate, cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, stearoamphoacetate, or mixtures thereof.

In a further embodiment, amphoteric surfactants, include, for example, derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include salts, typically alkali metal, alkaline earth metal, ammonium or substituted ammonium salts, of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, concentrated composition of the present invention additionally comprises one or more additional surfactants. The additional surfactants can be anionic, cationic or non-ionic. In a further embodiment, the additional surfactant can be a combination of any of an anionic surfactant, cationic surfactant or non-ionic surfactant.

In some embodiments, the anionic surfactant includes, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl(ether) phosphates, dialkyl(ether) phosphates, sarcosinates, sulfosuccinates, isethionates, and taurates, as well as mixtures thereof. Commonly used anionic surfactants that are suitable as the anionic surfactant component of the composition of the present invention include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl phosphate, sodium tridecyl phosphate, sodium behenyl phosphate, sodium laureth-2 phosphate, sodium ceteth-3 phosphate, sodium trideceth-4 phosphate, sodium dilauryl phosphate, sodium ditridecyl phosphate, sodium ditrideceth-6 phosphate, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate. Branched anionic surfactants are particularly preferred, such as sodium trideceth sulfate, sodium tridecyl sulfate, ammonium trideceth sulfate, ammonium tridecyl sulfate, and sodium trideceth carboxylate.

The cation of any anionic surfactant is typically sodium but may alternatively be potassium, lithium, calcium, magnesium, ammonium, or an alkyl ammonium having up to 6 aliphatic carbon atoms including isopropylammonium, monoethanolammonium, diethanolammonium, and triethanolammonium. Ammonium and ethanolammonium salts are generally more soluble that the sodium salts. Mixtures of the above cations may be used.

Suitable nonionic surfactants include alkoxylated alcohols, alkoxylated alkanolamides, alkoxylated fatty acids, and alkoxylated sorbitan derivatives and comprise from 1 mole to about 200 moles, more typically from 1 mole to about 100 moles, of $(C_2\text{-}C_4)$alkylene oxide units per mole of alkoxylated nonionic surfactant, wherein, on average, at least one alkoxyl unit per molecule of alkoxylated nonionic surfactant is a propoxyl unit. More typically, based on the total number of alkoxyl units of the alkoxylated nonionic surfactant, greater than 30%, more typically greater than 50%, even more typically greater than 80%, and still more typically greater than 99% of the alkoxyl units of the alkoxylated nonionic surfactant are propoxyl units.

Cationic surfactants are known. Any cationic surfactant that is acceptable for use in the intended end use application is suitable as the cationic surfactant component of the composition of the present invention, including, for example, mono-cationic surfactants according to formula (VIII) below:

(VIII)

wherein:

$R_1$, $R_2$, $R_3$ and $R_4$, are independently hydrogen, an organic group, provided that at least one of $R_1$, $R_2$, $R_3$ and $R_4$ is not hydrogen.

X is an anion.

If one to three of the R groups are hydrogen, the compound may be referred to as an amine salt. Some examples of cationic amines include polyethoxylated (2) oleyl/stearyl amine, ethoxylated tallow amine, cocoalkylamine, oleylamine, and tallow alkyl amine.

For quaternary ammonium compounds (generally referred to as quats) $R_1$, $R_2$, $R_3$, and $R_4$ may be the same or different organic group, but may not be hydrogen. In one embodiment, $R_1$, $R_2$, $R_3$, and $R_4$ are each $(C_8\text{-}C_{24})$ branched or linear alkyl, which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cetethyl morpholinium ethosulfate or steapyrium chloride.

Suitable anions include, for example, chloride, bromide, methosulfate, ethosulfate, lactate, saccharinate, acetate or phosphate.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl-dimethyl-(2)hydroxyethyl ammonium dihydrogen phosphate (also known as hydroxyethyl cetyldimonium phosphate), bassuamidopropylkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compound of the dialkyl amine derivative type distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Electrolytes suitable as an additional structurant component of the composition of the present invention include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulphonates or naphthalene sulphonate formaldehyde copolymers. Electrolytes may be added as a separate component of the structured surfactant or may be added as a part of another component of the composition, e.g., amphoteric surfactants, such as sodium lauroamphoacetate, typically contain an electrolyte, such as sodium chloride.

Nonionic surfactants include, for example, compounds produced by the condensation of alkylene oxide groups with an organic hydrophobic compound which may be aliphatic or alkyl aromatic in nature. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, and alkylpolyglycosides. Specific examples of suitable nonionic surfactants include alkanolamides such as cocamide DEA, cocamide MEA, cocamide MIPA, lauramide DEA, and lauramide MEA, alkyl amine oxides such as lauramine oxide, cocamine oxide, cocamidopropylamine oxide, and lauramidopropylamine oxide, sorbitan laurate, sorbitan distearate, fatty acids or fatty acid esters such as lauric acid, and isostearic acid, fatty alcohols or ethoxylated fatty alcohols such as lauryl alcohol, laureth-4, laureth-7, laureth-9, laureth-40, trideceth alcohol, C11-15 pareth-9, C12-13 Pareth-3, and C14-15 Pareth-11, alkylpolyglucosides such as decyl glucoside, lauryl glucoside, and coco glucoside.

The composition of the present invention may optionally further comprise one or more preservatives, such as benzyl alcohol, methyl paraben, propyl paraben, or imidazolidinyl urea, and DMDM hydantoin, and may optionally further comprise one or more pH adjusting agents, such as citric acid, succinic acid, phosphoric acid, sodium hydroxide, or sodium carbonate. The composition of the present invention may optionally further comprise one or more polymers and/or thickeners, chosen from the groups of clays, substituted or unsubstituted hydrocolloids, acrylate polymers, cationic polymers, hydrohobically modified nonionic polyols, and mixtures thereof. Some examples of clays include bentonite, kaolin, montmorillonite, sodium magnesium silicate, hectorite, magnesium aluminum silicate. Some examples hydrocolloids in the unmodified form include agar, alginate, arabinoxylan, carrageenan, cellulose derivatives, such as carboxyalkyl celluose, hydroxyalkyl cellulose, hydroxyalkyl alkyl cellulose, and alkyl cellulose, curdlan, gelatin, gellan, β-glucan, guar gum, gum arabic, locust bean gum, pectin, starch, succinoglycan, Xanthan gum. Some examples of modified or substituted hydrocolloids are hydroxy methyl cellulose, PG-hydroxyethyl cellulose, quaternary ammonium derivatives of hydroxyethyl cellulose, quaternary ammonium derivatives of guar gum (such as Jaguar C-17, Jaguar C-14S, Jaguar Excel, Jaguar C-162 from Rhodia), hydroxypropyl guars (Jaguar HP-8, Jaguar HP-105, Jaguar HP-60, Jaguar HP-120, Jaguar C-162), modified starches, such as sodium hydroxypropyl starch phosphate (Pure-Gel 980 and Pure-Gel 998 from Grain Processing Corporation), potato starch modified (such as Structure-Solanace from National Starch), acrylate copolymers such as acrylates/aminoacrylates/C10-30 alkyl PEG-20 itaconate copolymer (such as Structure-Plus from National Starch), cationic polymers (such as Rheovis CSP, Rheovis CDE, Rheovis CDP from Ciba), polyacrylimidomethylpropane Sulfonate/Polyquaternium-4 (Plexagel ASC from ISP), hydrohobically modified nonionic polyols (Acusol 880, Acusol 882 from Rohm & Haas), and PEG-150 distearate. In general, personal care compositions may optionally comprise, based on weight of the personal care composition and independently for each such ingredient, up to about 10 wt %, preferably from 0.01 wt % to about 5.0 wt %, of such other ingredients, depending on the desired properties of the personal care composition.

In another embodiment, the composition of the present invention may optionally comprise glycerine. Glycerine can be present in an amount between about 0.01 wt % to 2 wt %, by weight of the composition in one embodiment. In another embodiment, glycerine can be present in an amount between about 0.01 wt % to 1.5 wt %, by weight of the composition. In yet another embodiment, glycerine can be present in an amount between about 0.001 wt % to 1 wt %, by weight of the composition. In a further embodiment, glycerine can be present in an amount between about 0.001 wt % to 0.9 wt %, by weight of the composition. In another embodiment, glycerine can be present in an amount between about 0.001 wt % to 0.5 wt %, by weight of the composition.

In one embodiment, the pH of the composition of the present invention is less than 7, more typically within the range of from about 5 to less than 7, more typically, from about 5 to about 6.5.

In another embodiment, the pH of the composition of the present invention is greater than 7, more typically within the range of from about 8 to 11.5, more typically, from about 9 to about 11.

Low-temperature phase-stable concentrate compositions, in one embodiment, comprise an acyl glycinate present in an amount greater than a wt % as described herein, by weight of the composition; and at least one of (i) a zwitterionic surfactant or (ii) an amphoteric surfactant present in an amount greater than a wt % as described herein, by weight of the composition, wherein the concentrate is phase-stable at or below an ambient temperature as descried herein. In one embodiment, the acyl glycinate present in an amount greater than 20 or 21 wt %, by weight of the composition. In one embodiment, the at least one of (i) a zwitterionic surfactant or (ii) an amphoteric surfactant present in an amount greater than 0.1 wt %, 0.5 wt %, 0.8 wt % 1 wt %, 2 wt %, 3 wt %, 4 wt %, 5 wt %, by weight of the composition. In one embodiment, the concentrate is phase-stable at a temperature less than or equal to 20° C. In another embodiment, the concentrate is phase-stable at a temperature less than or equal to 10° C. In another embodiment, the concentrate is phase-stable at a temperature less than or equal to 8° C. In another embodiment, the concentrate is phase-stable at a temperature less than or equal to 4° C.

In another embodiment, low-temperature phase-stable concentrate compositions comprise an acyl glycinate present in an amount greater than a wt % as described herein, by weight of the composition; and one of: (i) a zwitterionic surfactant or (ii) an amphoteric surfactant present in an amount greater than a wt % as described herein, by weight of the composition, wherein the concentrate is phase-stable at or below an ambient temperature as descried herein. In one embodiment, the acyl glycinate present in an amount greater than 17 wt %, or 19 wt %, or 20 wt % or 21 wt %, by weight of the composition. In one embodiment, the (i) zwitterionic surfactant or (ii) amphoteric surfactant is present in an amount greater than 0.1 wt %, 0.5 wt %, 0.8 wt % 1 wt %, 2 wt %, 3 wt %, 4 wt %, 5 wt %, by weight of the composition. In one embodiment, the concentrate is phase-stable at a temperature less than or equal to 20° C. In one embodiment, glycerine is present in an amount between about 0.01 wt % to 2 wt %, by weight of the composition. In another embodiment, the concentrate is phase-stable at a temperature less than or equal to 10° C. In another embodiment, the concentrate is phase-stable at a temperature less than or equal to 8° C. In another embodiment, the concentrate is phase-stable at a temperature less than or equal to 4° C.

In yet another embodiment, low-temperature phase-stable concentrate compositions comprise an acyl glycinate present in an amount greater than a wt % as described herein, by weight of the composition; and a mixture of (i) a zwitterionic surfactant and (ii) an amphoteric surfactant present in an amount greater than a wt % as described herein, by weight of the composition, wherein the concentrate is phase-stable at or below an ambient temperature as descried herein. In one embodiment, the acyl glycinate present in an amount greater than 17 wt %, or 19 wt %, or 20 wt % or 21 wt %, by weight of the composition. In one embodiment, the mixture of (i) zwitterionic surfactant and (ii) amphoteric surfactant is present in an amount greater than 0.1 wt %, 0.5 wt %, 0.8 wt % 1 wt %, 2 wt %, 3 wt %, 4 wt %, 5 wt % by weight of the composition. In one embodiment, the concentrate is phase-stable at a temperature less than or equal to 20° C. In another embodiment, the concentrate is phase-stable at a temperature less than or equal to 10° C. In another embodiment, the concentrate is phase-stable at a temperature less than or equal to 8° C. In another embodiment, the concentrate is phase-stable at a temperature less than or equal to 4° C.

In some embodiments, the acyl glycinate is of formula (I):

$RC(O)NHCH_2CO_2X$                                              (I), wherein R is a $C_9$-$C_{23}$ alkyl Group, and X is a cation or H. The cation can be any suitable cation, including but not limited to, sodium, potassium, or ammonium. The R group is, in one embodiment, a $C_8$-$C_{18}$ group, while in other embodiments, R is a C10-C14 group.

The at least one zwitterionic surfactant or amphoteric surfactant can be an alkyl betaine surfactant or an alkyl sulfobetaine surfactant. In some embodiments, the zwitterionic surfactant or amphoteric surfactant component can be a combination of both alkyl betaine surfactant and alkyl sulfobetaine surfactant. The zwittionic and/or amphoteric surfactants are useful not only in lowering the temperature at which the concentrated composition remains phase-stable, but are also useful in imparting desirable cleansing and feel properties to any resulting formulation. Ingredients that are commonly used to, for example, lower freezing point of a composition are not useful for imparting cleansing, foaming and feel properties in resulting home and personal care applications and products. Ingredients that are commonly used to lower freezing point of a composition, for example, solvents such as propylene glycol, are not useful for imparting cleansing, foaming and feel properties in resulting home and personal care applications and products.

A concentrated acyl glycinate composition can be made phase-stable at a low temperature upon contact with a zwitterionic surfactant or amphoteric surfactant, as described herein. In one embodiment, one can impart low temperature phase-stability to a concentrated acyl glycinate composition by contacting a surfactant component comprising at least one of a zwitterionic surfactant or an amphoteric surfactant to the concentrated acyl glycinate composition, forming a resulting mixture. The concentrated acyl glycinate composition comprises acyl glycinate in an amount greater than 10 wt %, by weight of the composition, whereby the resulting mixture is stable at temperature of less than 10° C. In one embodiment, the surfactant component is present in an amount greater than 0.1% by weight of resulting mixture. In another embodiment, the surfactant component is present in an amount greater than 1% by weight of resulting mixture. In another embodiment, the surfactant component is present in an amount greater than 4% by weight of resulting mixture.

In one embodiment, the surfactant component is selected from an alkyl betaine surfactant, an alkyl sulfobetaine surfactant or a mixture thereof. R can be a $C_8$-$C_{18}$ group or, in other embodiment, R is a $C_{10}$-$C_{14}$ group. In some embodiments, the cation is selected from sodium, potassium, or ammonium.

In another embodiment, one can impart low temperature phase-stability to a concentrated acyl glycinate composition by first obtaining a concentrated acyl glycinate composition comprising greater than 10 wt %, by weight of composition, of acyl glycinate; then contacting a surfactant component comprising at least one of a zwitterionic surfactant or an amphoteric surfactant to the concentrated acyl glycinate composition, forming a resulting mixture.

Further, as described herein are methods of imparting freeze-thaw stability to an acyl glycinate concentrate composition comprising the steps of:
    obtaining an acyl glycinate concentrate composition comprising acyl glycinate in an amount greater than 10 wt %, by weight of the composition; and
    contacting the acyl glycinate concentrate composition with a surfactant component comprising at least one of a zwitterionic surfactant or an amphoteric surfactant,
    wherein the surfactant component is present in an amount greater than 0.1% by weight of the composition, effective to impart freeze-thaw stability to the composition.

The surfactant component, in one embodiment, is present in an amount greater than 1% by weight of the composition. In other embodiments, the surfactant component is present in an amount greater than 2% by weight of the composition. In yet another embodiment, the surfactant component is present in an amount greater than 3% by weight of the composition. In a further embodiment, the surfactant component is present in an amount greater than 4% by weight of the composition. The surfactant component is typically at least one of an alkyl betaine surfactant, an alkyl hydroxyl sulfobetaine surfactant, an alkyl sulfobetaine surfactant, or any salts thereof.

In one embodiment, a personal or home care composition is made by diluting the concentrated acyl glycinate composition of the present invention with water and additional components as described herein.

The composition of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the concentrate composition of the present invention is incorporated into a personal care composition.

In one embodiment, the personal care composition of the present invention comprises the concentrated acyl glycinate composition of the present invention in combination with additional water and/or one or more additional ingredients and suitable personal care compositions are made by diluting the concentrated acyl glycinate composition with water and/or mixing the composition with additional ingredients.

In one embodiment, the personal care composition further comprises one or more benefit agents, such as emollients, moisturizers, conditioners, skin conditioners, hair conditioners, vitamins or their derivatives, antioxidants, free-radical scavengers, abrasives, dyes, hair coloring agents, bleaching agents, hair bleaching agents, anti-UV agents, UV absorbers, antimicrobial agents, antibacterial agents, antifungal agents, melanin regulators, tanning accelerators, depigmenting agents, skin-coloring agents, liporegulators, weight-reduction agents, anti-acne agents, antiseborrhoeic agents, anti-ageing agents, anti-wrinkle agents, keratolytic agents, anti-inflammatory agents, refreshing agents, cicatrizing agents, vascular-protection agents, antiperspirants, deodorants, immunomodulators, nourishing agents, agents for combating hair loss, reducing agents for permanent-waving, essential oils and fragrances.

The personal care composition according to the present invention may optionally further comprise other ingredients, such as, for example, preservatives such as benzyl alcohol, methyl paraben, propyl paraben and imidazolidinyl urea, thickeners and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate.

The personal care composition of the present invention is used in a manner know in the art, for example, in the case of a cleanser or shampoo, by application of the cleanser or shampoo to the skin and/or hair and optionally rinsing the cleanser or shampoo off of the skin and/or hair with water.

EXAMPLES

Sodium cocoyl glycinate and sodium lauryl glycinate concentrates were tested incorporating betaines and sulfobetaines, as shown in the following tables. Table I illustrates the samples utilized in testing. Table II illustrates the observed properties of lauryl cocoyl glycinate, by itself, and compared with blends incorporating betaines and sulfobetaines (on an active weight % basis). Table III corresponds to observed properties of sodium lauryl glycinate, by itself, and compared with blends incorporating betaines and sulfobetaines (on an active weight % basis).

TABLE 1

|  | Sample# | NaCl (%) | Active (%) | FFA | Glycine |
|---|---|---|---|---|---|
| Cocamidopropyl Betaine | WI1E22X04 | 4.9 | 30.4 |  |  |
| Cocamidopropyl Hydroxy Sultaine | UP3C28X16 | 6.1 | 43.2 |  |  |
| Lauryl glycinate | SW12L4803 | 4.9 | 20.8 | 1 | 0.7 |
| Coco Glycinate | WI3A15X03 | 5.3 | 22.9 | 0.9 | 1 |

TABLE II

| Cocoyl Glycinate (WI3A15X03) | | | | | | | |
|---|---|---|---|---|---|---|---|
|  | WI3A15X03 | R095718 7-2-1 | R095718 7-2-2 | R095718 7-2-3 | R1078-017-13-1 | R1078-017-13-2 | R1078-017-13-3 |
| wt % active Glycinate | 22.9 | 22.2 | 21.5 | 20.6 | 22.2 | 21.5 | 20.6 |
| wt % active Betaine WI1E22X04 | 0 | 1 | 2 | 3.5 |  |  |  |
| wt % active Sultaine UP3C28X16 | 0 |  |  |  | 1 | 2 | 4 |
| First sign of turbidity ° C. | 17 | 10 | 8 | <6 | 10 | <6 | <6 |
| Uniform White Liquid ° C. | 14 | 7 | 6 | Clear Liquid | 7 | Clear Liquid | Clear Liquid |
| Freeze Temp ° C. | 13 | 4 | <4 | <4 | <4 | <4 | <4 |
| % NaCl (total) | 5.3 |  |  |  |  |  |  |
| % Actives (total) | 22.9 | 23.1 | 23.5 | 24.1 | 23.1 | 23.5 | 24.6 |
| Appearance Frozen State | White Solid | White Solid | White Solid | White Solid | White Solid | White Solid | Clear Solid |
| Appearance 4° C. | White Solid | White Solid | Pearl L | Pearl L | Opaque Liquid | Clear Liquid | Clear Liquid |
| F/T Appearance @ RT | Clear/ Precip. | Clear Liquid | Clear Liquid | Clear Liquid | Clear Liquid | Clear Liquid | Clear Liquid |
| 4° C. Appearance @ RT | Clear/ Precip. | Clear Liquid | Clear Liquid | Clear Liquid | Clear Liquid | Clear Liquid | Clear Liquid |

As seen in Table II, cocoyl glycinate by itself shows signs of reaching phase instability, i.e., signs of turbidity, at a higher temperature as compared with glycinates blends incorporating betaine and/or hydroxy sultaine surfactant(s). Additional, after one F/T cycle, the cocoyl glycinate by itself does not recover from its unfrozen states, as precipitates are observed. Cocoyl glycinates blends incorporating betaine and/or hydroxy sultaine surfactant(s) were observed as a clear liquid after one F/T cycle.

Similar results were shown when cocoyl glycinate was blended with a laurylamphoacetate salt, i.e., observed as a clear liquid after one F/T cycle and observed signs of turbidity at lower temperatures, as opposed to cocoyl glycinates by itself.

TABLE III

| | Lauryl Glycinate | | | | | | |
|---|---|---|---|---|---|---|---|
| Notebook # | SW12L4803 | R0992-058-01 | R0992-058-02 | R0992-058-03 | R0992-058-04 | R0992-058-05 | R0992-058-06 |
| wt % active Glycinate | 20.8 | 20.4 | 20.2 | 19.6 | 20.4 | 20.0 | 19.1 |
| wt % active Betaine WI1E22X04 | 0 | 0.6 | 0.9 | 1.8 | | | |
| wt % active Sultaine UP3C28X16 | 0 | | | | 0.9 | 1.7 | 3.5 |
| % NaCl (total) | 5.4 | 5.4 | 5.3 | 5.4 | 5.4 | 5.4 | 5.5 |
| % Actives (total) | 21.0 | 21.4 | 21.2 | 21.4 | 21.4 | 21.7 | 23.3 |
| First sign of turbidity ° C. | 11 | 7.5 | 7 | 0.5 | 7.0 | 1.5 | −4.5 |
| Uniform White Liquid ° C. | 9 | 5.4 | 4 | −1 | 5.0 | 0.8 | −5.5 |
| Freeze Temp ° C. | <0 | <0 | <0 | <0 | <0 | <0 | <0 |
| Appearance Frozen State | White Solid | White Solid | White Solid | White Solid | Crystal/solid | Crystal/solid | Crystal/solid |
| Appearance 4° C. | Slushy/opaque | 2 phase/Clear: white solid | 2 phase/Clear: white solid | 2 phase/Clear: white solid | Slush/opaque | Froze/White | Froze/White |
| F/T Appearance @ RT | Clear/Precip. | Clear/Precip. | Clear/Precip. | Clear/Precip. | White solid | White solid | White solid |
| 4° C. Appearance @ RT | Clear/Precip. | Clear/Precip. | Clear/Precip. | Clear/Precip. | Clear/Precip. | Clear/Precip. | Clear/Precip. |

As seen in Table III, lauryl glycinate by itself shows signs of reaching phase instability, i.e., signs of turbidity, at a higher temperature as compared with glycinates blends incorporating betaine and/or hydroxy sultaine surfactant(s).

What is claimed is:

1. A low-temperature phase-stable concentrate composition consisting of:
   a) an acyl glycinate present in an amount greater than 15 wt %;
   b) at least one of a zwitterionic surfactant or an amphoteric surfactant present in an amount greater than about 0.1 wt %; and
   (c) water; and, optionally,
   (d) glycerine in an amount from about 0.01 wt % to about 2 wt %; and, optionally,
   (e) at least one electrolyte,
   wherein the amounts are by total weight of the composition and
   wherein the concentrate is phase-stable at a temperature less than or equal to 17° C.

2. The concentrate composition of claim 1 wherein the acyl glycinate is of formula (1):

RC(O)NHCH$_2$CO$_2$X    (I), wherein R is a C$_8$-C$_{22}$ alkyl group, and X is a cation or H.

3. The concentrate composition of claim 2 wherein the cation is selected from sodium, potassium, or ammonium.

4. The concentrate of claim 2 wherein R is a C$_8$-C$_{18}$ group.

5. The concentrate of claim 1 wherein the at least one zwitterionic surfactant or amphoteric surfactant is selected from an alkyl betaine surfactant or salt thereof, an alkyl hydroxyl sulfobetaine surfactant or salt thereof, or an alkyl sulfobetaine surfactant or salt thereof.

6. The concentrate of claim 1 wherein the at least one zwitterionic surfactant or amphoteric surfactant is an alkyl sulfobetaine surfactant or salt thereof.

7. The concentrate of claim 1 wherein the at least one zwitterionic surfactant or amphoteric surfactant is present in an amount greater than 0.5 wt % by weight of the composition.

8. The concentrate of claim 1 wherein the at least one zwitterionic surfactant or amphoteric surfactant is present in an amount greater than 1 wt % by weight of the composition.

9. The concentrate of claim 1 wherein the at least one zwitterionic surfactant or amphoteric surfactant is selected from alkyl betaines or salts thereof, amidopropyl betaines or salts thereof, alkyl sulfobetaines or salts thereof, alkyl amphocarboxy glycinates or salts thereof, alkyl amphocarboxypropionates or salts thereof, alkyl amphodipropionates or salts thereof, alkyl amphoglycinates or salts thereof, alkyl amphopropionates or salts thereof, alkyl iminopropionates or salts thereof, alkyl iminodipropionates or salts thereof, alkyl amphopropylsulfonates or salts thereof, or mixtures thereof.

10. The concentrate of claim 1 wherein the concentrate is phase-stable at a temperature less than or equal to 6° C.

11. The concentrate of claim 1 wherein the concentrate is phase-stable at a temperature less than or equal to 4° C.

12. A method for storing a concentrated acyl glycinate composition by:
   a) obtaining a concentrated acyl glycinate composition consisting of water and greater than 15 wt %, by total weight of composition, of acyl glycinate; and
   b) contacting at least one of a zwitterionic surfactant or amphoteric surfactant component with the concentrated acyl glycinate composition, whereby the concentrated acyl glycinate composition is phase-stable at a temperature less than or equal to 17° C.

13. The method of claim 12 wherein the surfactant component is present in the concentrated acyl glycinate composition in an amount greater than 0.5 wt % by weight of composition.

14. The method of claim 12 wherein the surfactant component is present in the concentrated acyl glycinate composition in an amount greater than 1 wt % by weight of composition.

15. The method of claim 12 wherein the surfactant component is present in the concentrated acyl glycinate composition in an amount greater than 25 wt % by weight of composition.

16. The method of claim 12 wherein the surfactant component is selected from an alkyl betaine surfactant, an alkyl sulfobetaine surfactant or a mixture thereof.

17. The method of claim 12 wherein the acyl glycinate is of formula (I):

wherein R is a $C_8$-$C_{22}$ alkyl group, and X is a cation or H.

18. The method of claim 12 whereby the concentrated acyl glycinate composition is phase-stable at a temperature less than or equal to 10° C.

19. The method of claim 12 whereby the concentrated acyl glycinate composition is phase-stable at a temperature less than or equal to 4° C.

* * * * *